US00PP09238P

United States Patent [19]

Tas

[11] Patent Number: Plant 9,238

[45] Date of Patent: Aug. 8, 1995

[54] MAIDENHAIR FERN PLANT NAMED 'BRONZE VENUS'

[75] Inventor: Wim P. Tas, Aalsmeer, Netherlands

[73] Assignee: Milestone Agriculture, Inc., Apopka, Fla.

[21] Appl. No.: 321,823

[22] Filed: Oct. 6, 1994

[51] Int. Cl.[6] ..... A01H 5/00

[52] U.S. Cl. ..... Plt./88.3

[58] Field of Search ..... Plt. 88.3

*Primary Examiner*—James R. Feyrer

[57] ABSTRACT

A distinct cultivar of Fern plant named Bronze Venus, characterized by its fronds that are light brown when immature, turning light green as they mature, and darker green when mature giving plants of Bronze Venus a tricolor appearance; symmetrical plant habit; arching plant shape; numerous pinnules, pinnae and fronds that form a dense plant canopy; large, spreading, pedate fronds; long narrow pinnules with finely serrated abaxial margins giving plants of Bronze Venus a feathery appearance; and rapid growth rate.

1 Drawing Sheet

The present invention relates to a new and distinct cultivar of Fern, botanically known as *Adiantum pubescens*, and hereinafter referred to by the cultivar name Bronze Venus.

The new cultivar was discovered by me at Fernselect B.V., Aalsmeer, Holland, as a naturally occurring sport or mutation in a population of 50 plants of the species *Adiantum pubescens*.

Asexual reproduction of the new cultivar by tissue culture propagation at Fernselect B.V., Aalsmeer, Holland, has shown that the unique features of this new Fern are firmly fixed and retained through twelve successive generations of asexual reproduction.

The cultivar Bronze Venus has not been observed under all possible environmental conditions. The phenotype may vary significantly with variations in environment such as temperature and light intensity. The following observations, measurements and comparisons describe plants grown in Apopka, Fla., under conditions generally used in commercial practice.

The following traits have been repeatedly observed and are determined to be the unique characteristics of Bronze Venus. These characteristics in combination distinguish Bronze Venus as a new and distinct cultivar:

1. Fronds that are light brown when immature, turning light green as they mature, and darker green when mature giving plants of Bronze Venus a tricolor appearance.
2. Symmetrical plant habit.
3. Arching plant shape.
4. Numerous pinnules, pinnae and fronds that form a dense plant canopy.
5. Large, spreading pedate fronds.
6. Long narrow pinnules with finely serrated abaxial margins giving plants of Bronze Venus a feathery appearance.
7. Rapid growth rate.

Bronze Venus is most similar to its parent cultivar, the species *Adiantum pubescens*. Bronze Venus differs from the species *Adiantum pubescens* in the following characteristics:

1. Fronds of Bronze Venus that are intermediate in development are lighter green than fronds of *Adiantum pubescens* that are intermediate in development. Fronds of *Adiantum pubescens* that are intermediate in development are the same darker green color as mature fronds. The lighter green color of the intermediate fronds gives plants of Bronze Venus a tricolor appearance compared to the bicolor appearance of plants of *Adiantum pubescens*.

2. Plants of Bronze Venus are more symmetrical in plant habit than plants of *Adiantum pubescens*.

3. Fronds of plants of both Bronze Venus and *Adiantum pubescens* are erect when young. As fronds of plants of Bronze Venus develop, they become more outwardly arching. As fronds of plants of *Adiantum pubescens* develop, they become pendant.

4. Plants of Bronze Venus are larger than plants of *Adiantum pubescens* as front length and width of plants of Bronze Venus are greater than the frond length and width of plants of *Adiantum pubescens*.

5. Fronds of Bronze Venus are more feathery in appearance than fronds of *Adiantum pubescens* as pinnules of Bronze Venus are longer, narrower and their abaxial margins are more finely serrated than pinnules of *Adiantum pubescens*.

6. Pinnules of Bronze Venus appear less glossy than pinnules of *Adiantum pubescens*. Bronze Venus pinnules are sparsely pubescent and *Adiantum pubescens* pinnules are glabrous.

7. Plants of Bronze Venus have more pinnules per pinna compared to plants of *Adiantum pubescens*.

8. Pinnule tip shape on plants of Bronze Venus is acute compared to rounded pinnule tip shape on plants of *Adiantum pubescens*.

9. Pinnule aspect is different, that is, pinnules of plants of Bronze Venus are flat, and pinnules to *Adiantum pubescens* are cupped upwardly.

10. Pinnule arrangement is different, that is, pinnules of plants of Bronze Venus do not overlap, and pinnules of plants of *Adiantum pubescens* overlap slightly.

A detailed comparison of Bronze Venus and *Adiantum pubescens* plants appears in Chart A at the end of the specification.

The accompanying colored photograph illustrate the overall appearance of the new cultivar, showing the colors as true as it is reasonably possible to obtain in colored reproductions of this type. The photograph comprises a top perspective view of a typical potted plant of Bronze Venus.

In the following description, color references are made to The Royal Horticultural Society Colour Chart except where general terms of ordinary dictionary significance are used. Measurements and numerical values represent averages for six typical plants.

Botanical classification: *Adiantum pubescens* cultivar Bronze Venus.

Parentage: Naturally occurring sport or mutation of the species *Adiantum pubescens.*

Propagation: By tissue culture.

Rooting habit: Rhizomes are fibrous, well-branched and aggressive. Tissue culture plantlets develop rhizomes within 7 days under warm (80° F.) conditions, and within 10 days under cooler (70° F.) conditions.

Plant Description

A. Plant shape: Triangular (inverted), symmetrical.

B. Growth habit: Erect when young, becoming outwardly arching as fronds develop. Maintains compact size over time. Appropriate for small and large pots.

C. Plant height: 17.5 cm from soil line to top of plant plane.

D. Plant width: 44 cm in diameter.

E. Plant vigor: Moderately high.

F. Frond description:

1. *Frond shape/arrangement.*—Spreading, pedate, 3 to 5-pinnate.
2. *Frond length.*—30 cm.
3. *Frond width.*—17 cm.
4. *Quantity of fronds.*—Many, moderately dense plant form.
5. *Petiole length.*—14 cm.
6. *Petiole color.*—a. Immature: 175A. b. Intermediate: 187A. c. Mature: 202A.
7. *Petiole texture.*—Rough, pubescent.

G. Pinnae description:

1. *Arrangement.*—One-pinnate.
2. *Shape.*—Narrow, lanceolate.
3. *Middle pinna (rachis) length.*—16 cm.
4. *Middle pinna width.*—3.5 cm.
5. *Rachis color.*—a. Immature: 175A. b. Intermediate: 187A. c. Mature: 202A.

H. Pinnule description:

1. *Pinnule shape.*—Narrow, rhombic.
2. *Pinnule length.*—16.5 mm.
3. *Pinnule width.*—7 mm.
4. *Quantity of pinnules per middle pinna.*—47.
5. *Margin.*—a. Abaxial: Very finely serrated, feathered. b. Adaxial: Entire.
6. *Number of lobes.*—Numerous.
7. *Pinnule tip.*—Shaprly acute, pointed.
8. *Pinnule base.*—Truncate.
9. *Pinnule aspect.*—Flat, perpendicular to stem.
10. *Pinnule arrangement.*—Not overlapping.
11. *Pinnule attachment.*—Stalked, very small petiole.
12. *Pinnule texture.*—Slightly rippled, slightly raised venation, sparsely pubescent.
13. *Pinnule color.*—a. Immature, top side: 174A. b. Immature, under side: 165A. c. Intermediate, top side: 146C to 146B. d. Intermediate, under side: 146C to 146B. e. Mature, top side: Greener than 146A. f. Mature, under side: Greener than 146A.
14. *Venation pattern.*—Palmate.

I. Sori description:

1. *Arrangement.*—Marginal.
2. *Sori shape.*—Rounded.
3. *Sori color.*—175A.

Disease resistance: No resistance nor susceptibility to pathogens has been noted.

CHART A

| CHARACTERISTIC | BRONZE VENUS | *ADIANTUM PUBESCENS* |
|---|---|---|
| PLANT SHAPE | Triangular (inverted) Symmetrical | Triangular (inverted) Not symmetrical |
| GROWTH HABIT | Erect when young Outwardly arching as fronds develop | Erect when young Pendant as fronds develop |
| PLANT HEIGHT | 17.5 cm | 15.5 cm |
| PLANT WIDTH | 44 cm | 29 cm |
| SUITABLE CONTAINER(S) | Pots | Pots |
| FROND SHAPE/ ARRANGEMENT | Spreading Pedate, 3 to 5-pinnate | Spreading Pedate, 3 to 5-pinnate |
| FROND LENGTH | 30 cm | 26.5 cm |
| FROND WIDTH | 17 cm | 11 cm |
| QUANTITY OF FRONDS | Many, moderately dense plant form | Many, moderately dense plant form |
| PETIOLE LENGTH | 14 cm | 13 cm |
| PETIOLE/RACHIS COLOR, IMMATURE | 175A | 175A |
| PETIOLE/RACHIS COLOR, INTERMEDIATE | 187A | 187A |
| PETIOLE/RACHIS COLOR, MATURE | 202A | 202A |
| MIDDLE PINNA (RACHIS) LENGTH | 16 cm | 13.5 cm |
| MIDDLE PINNA WIDTH | 3.5 cm | 2.5 cm |
| PINNULE LENGTH | 16.5 mm | 11.5 mm |
| PINNULE WIDTH | 7 mm | 8 mm |
| QUANTITY OF PINNULES PER MIDDLE PINNA | 47 | 39 |
| PINNULE MARGIN | Abaxial: Very finely serrated Adaxial: Entire | Abaxial: Crenate Adaxial: Entire |
| NUMBER OF LOBES | Numerous | Numerous |
| PINNULE TIP | Sharply acute, pointed | Rounded |
| PINNULE BASE | Truncate | Truncate |
| PINNULE ASPECT | Flat Perpendicular to stem | Slightly cupped upward |
| PINNULE ARRANGEMENT | Not overlapping | Overlap slightly |
| PINNULE ATTACHMENT | Stalked, very small petiole | Stalked, very small petiole |
| PINNULE TEXTURE | Slightly rippled, slight raised venation Sparsely pubsecent | Rippled, prominent venation Glabrous |
| PINNULE COLOR, IMMATURE, TOP SIDE | 174A | 175A |
| PINNULE COLOR, IMMATURE, UNDER SIDE | 165A | 175A |
| PINNULE COLOR INTERMEDIATE, TOP SIDE | 146C to 146B | Greener than 146A |
| PINNULE COLOR, INTERMEDIATE, UNDER SIDE | 146C TO 146B | Greener than 146A |
| PINNULE COLOR, MATURE, TOP SIDE | Greener than 146A | Greener than 146A |
| PINNULE COLOR, MATURE, UNDER SIDE | Greener than 146A | Greener than 146A |

I claim:

1. A new and distinct cultivar of Fern plant named Bronze Venus, as illustrated and described.

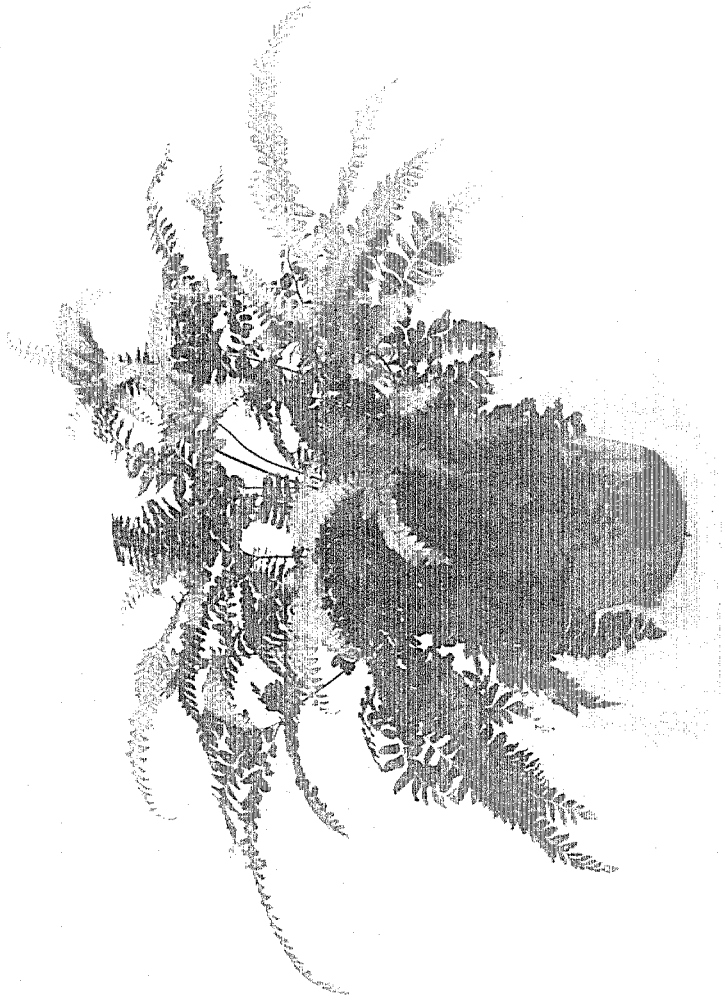

* * * * *